United States Patent
Ray et al.

(10) Patent No.: US 7,038,041 B2
(45) Date of Patent: May 2, 2006

(54) SELECTIVE NUCLEAR RECEPTOR-TARGETED SYSTEMS FOR DELIVERY OF CYTOTOXINS TO CANCER CELLS FOR TARGETED PHOTODYNAMIC THERAPY

(75) Inventors: Rahul Ray, Wayland, MA (US); Scott C. Mohr, Wellesley, MA (US); Narasimha Swamy, Providence, RI (US)

(73) Assignee: The Trustees of Boston University, Boston, MA (US)

( * ) Notice: Subject to any disclaimer, the term of this patent is extended or adjusted under 35 U.S.C. 154(b) by 292 days.

(21) Appl. No.: 10/257,081

(22) PCT Filed: Apr. 12, 2001

(86) PCT No.: PCT/US01/12196

§ 371 (c)(1),
(2), (4) Date: Nov. 7, 2002

(87) PCT Pub. No.: WO01/78606

PCT Pub. Date: Oct. 25, 2001

(65) Prior Publication Data

US 2003/0220313 A1    Nov. 27, 2003

Related U.S. Application Data

(60) Provisional application No. 60/196,637, filed on Apr. 12, 2000.

(51) Int. Cl.
C07D 487/22    (2006.01)
C07D 209/00    (2006.01)
A61K 31/555    (2006.01)

(52) U.S. Cl. ............... 540/145; 552/502; 514/185; 514/169; 514/170; 514/171; 514/182; 514/179; 534/15; 435/2

(58) Field of Classification Search ............ 540/145; 552/502; 514/169, 170, 171, 182, 179, 185
See application file for complete search history.

(56) References Cited

U.S. PATENT DOCUMENTS 5,272,142 A * 12/1993 Sessler et al. ............ 514/185
5,703,230 A * 12/1997 Boyle et al. ............. 540/145
6,444,194 B1 * 9/2002 Robinson et al. ......... 424/9.61

FOREIGN PATENT DOCUMENTS

WO    WO 9616966 A1 *  6/1996

OTHER PUBLICATIONS

Boyle et al., Iodination and Heck alkynylation of 5,15,-diphenylporphyrin., Journal of the Chemical Society, Chemical Communications (1995), (5), 527-8, AN 1995: 450120 HCAPLUS, DN 122:314331.*
Shanmugathasan et al., Regioselective halogenation and palladium-catalysed couplings on 5,15-diphenylporphyrin, Journ of Porphyrins and Phthalocyanines (2000), 4(3), 228-232, AN 2000:251139 HCAPLUS, DN 132:347438.*
Chen et al., "Chemical Studies of Estrogenic Steriod-Porphyrins, Part III, Synthesis of Estrogenic Steroid-Porphyrins and Their Metal Complexes", Youji Huaxue, May 1992, vol. 12, No. 1, pp 102-106.
Chen et al., Chemistry of Steroid-Porphyrins. I Synthesis of Steroid-Porphyrins Compounds, Youji Huaxue, Oct. 12, 1998, vol. 8, No. 1, pp 34-36.
Boyle et al., Iodination and Heck Alkylation of 5,15-diphenylporphyrin. A Convenient Entry to Asymmetrically Meso-substituted Porphyrins, J. Chem Soc. Commun, 1995, vol. 5, pp 527-528.

* cited by examiner

*Primary Examiner*—Sabiha Qazi
(74) *Attorney, Agent, or Firm*—Weingarten, Schurgin, Gagnebin & Lebovici LLP

(57) ABSTRACT

An estrogen/antiestrogen-porphyrin conjugate, their composition and methods for their use are claimed. The active compounds of the invention are conjugates consisting of an estrogen or anti estrogen portion, tether or linker portion and a porphyrin portion. The method of invention exploits an active process that involves strong and specific interactions between nuclear receptor and its cognate ligand.

18 Claims, 12 Drawing Sheets

Scheme for the synthesis of C17- ∝ethynyl -porphyrin conjugates (Compounds B-E)

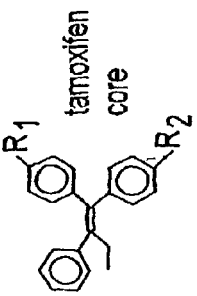

$R_1 = X-Y-(CH_2)_n-X-Y-P$, where $X = O, NH, S; Y = C(=O), C(=S), n = 1-20, R_2, R_3 = H$, or
$R_1 = X-Y-(CH_2)_n-Y-X-P$, where $X = O, NH, S; Y = C(=O), C(=S), n = 1-20, R_2, R_3 = H$, or
$R_1 = Z-(CH_2)_n-X-Y-P$, where $X = O, NH, S; Y = C(=O), C(=S); Z = C≡C, C=CH, CH_2-CH_2, n = 1-20, R_2, R_3 = H$, or $R_2 = X-Y-(CH_2)_n-X-Y-P$, where $X = O, NH, S; Y = C(=O), C(=S), n = 1-20, R_1, R_3 = H$, or
$R_2 = X-Y-(CH_2)_n-Y-X-P$, where $X = O, NH, S; Y = C(=O), C(=S), n = 1-20, R_1, R_3 = H$, or
$R_2 = Z-(CH_2)_n-X-Y-P$, where $X = O, NH, S; Y = C(=O), C(=S); Z = C≡C, C=CH, CH_2-CH_2, n = 1-20, R_1, R_3 = H$, or, $R_3 = X-Y-(CH_2)_n-X-Y-P$, where $X = O, NH, S; Y = C(=O), C(=S), n = 1-20, R_1, R_2 = H$, or
$R_3 = X-Y-(CH_2)_n-Y-X-P$, where $X = O, NH, S; Y = C(=O), C(=S), n = 1-20, R_1, R_2 = H$, or
$R_3 = Z-(CH_2)_n-X-Y-P$, where $X = O, NH, S; Y = C(=O), C(=S); Z = C≡C, C=CH, CH_2-CH_2, n = 1-20, R_1, R_2 = H$, $R_1 = O-(CH_2)_2-N(CH_3)_2, R_2 = X-Y-(CH_2)_n-X-Y-P$, where $X = O, NH, S; Y = CH_2, C(=O), C(=S), n = 1-20, R_2 = H, OH$, or
$R_1 = O-(CH_2)_2-N(CH_3)_2, R_2 = X-Y-(CH_2)_n-Y-X-P$, where $X = O, NH, S; Y = C(=O), C(=S), n = 1-20$, or
$R_1 = O-(CH_2)_2-N(CH_3)_2, R_2 = Z-(CH_2)_n-X-Y-P$, where $X = O, NH, S; Y = C(=O), C(=S); Z = C≡C, C=CH, CH_2-CH_2, n = 1-20$, or $R_1 = X-Y-(CH_2)_n-X-Y-P$, where $X = O, NH, S; Y = CH_2, C(=O), C(=S), n = 1-20, R_2 = H, OH$, or
$R_1 = X-Y-(CH_2)_n-Y-X-P$, where $X = O, NH, S; Y = C(=O), C(=S), n = 1-20, R_2 = H, OH$, or
$R_1 = Z-(CH_2)_n-X-Y-P$, where $X = O, NH, S; Y = C(=O), C(=S); Z = C≡C, C=CH, CH_2-CH_2, n = 1-20, R_2 = H, OH$ $R_1 = O-(CH_2)_2-N(CH_3)_2-W)CH_3$, where $W = X-Y-(CH_2)_n-X-Y-P$, where $X = O, NH, S; Y = CH_2, C(=O), C(=S), n = 1-20, R_2 = H, OH$, or
$R_1 = O-(CH_2)_2-N(CH_2-W)CH_3$, where $W = X-Y-(CH_2)_n-Y-X-P$, where $X = O, NH, S; Y = C(=O), C(=S), n = 1-20, R_2 = H, OH$, or
$R_1 = O-(CH_2)_2-N(CH_2-W)CH_3$, where $W = Z-(CH_2)_n-X-Y-P$, where $X = O, NH, S; Y = C(=O), C(=S); Z = C≡C, C=CH, CH_2-CH_2, n = 1-20,$
$R_2 = H, OH$ P = Porphyrin derivatives, natural or synthetic, with the general structure shown above

FIG. 11

SELECTIVE NUCLEAR RECEPTOR-TARGETED SYSTEMS FOR DELIVERY OF CYTOTOXINS TO CANCER CELLS FOR TARGETED PHOTODYNAMIC THERAPY

CROSS REFERENCE TO RELATED APPLICATIONS

This application claims the priority of U.S. Provisional Application No. 60/196,637 filed Apr. 12, 2000 entitled, DEVELOPMENT OF SELECTIVE NUCLEAR RECEPTOR-TARGETED SYSTEMS TO DELIVER CYTOTOXINS, INCLUDING PHOTOSENSITIZERS, TO CANCER CELLS FOR TARGETED PHOTODYNAMIC THERAPY, the whole of which is hereby incorporated by reference herein.

STATEMENT REGARDING FEDERALLY SPONSORED RESEARCH OR DEVELOPMENT

This invention was made with United States Government Support under Contract Number DK 47418 awarded by the National Institutes of Health. Therefore, the U.S. Government has certain rights in the invention.

BACKGROUND OF THE INVENTION

Photodynamic therapy (PDT), a recently developed method of intervention in the treatment of cancer, is based on the systemic administration of certain photosensitizing dyes, e.g. psoralens, pthalocyanins, acridine orange, and porphyrins in a manner that results in their selective accumulation into rapidly-proliferating cancer cells and the subsequent exposure of the tumor to light from a tunable laser, to kill the tumor (1,2). The dyes, due to their photosensizing nature, capture photons from the light and transfer the energy to a neighboring oxygen molecule. This secondary reaction converts oxygen molecules to highly cytotoxic singlet oxygen, which leads to the death of the tumor cells. Since the irradiation is carried out at a wavelength of 600–800 nm, and singlet oxygen can travel only 0.1–0.2 μm from its site of generation, little damage occurs to the surrounding healthy tissues.

The above description, however, is somewhat of an idealized situation because (a) selective accumulation of the PDT dyes solely by tumor cells is often difficult to achieve, (b) normal cells are also capable of accumulating porphyrins, and (c) the excretion of porphyrins from tissue is often slow. Clinically, these problems are often countered by the administration of a high dose of the dye, which can cause killing of the healthy cells surrounding the malignant tissues and prolonged toxicity of large body areas toward light-exposure.

Despite these problems, PDT has been applied to malignancies of esophagus (3), bladder (4), eye (5,6), and skin (7,8) with very encouraging results. A positive response to PDT that lasted at least four months was achieved in treatment of a malignancy of the eye (6). Additionally, response rates of up to 80% have been observed in basal cell carcinomas (9,10). In a recent study involving an EMT-6 mammary tumor model, a 100% cure rate was observed using a combination of PDT dyes (2). The porphyrin dye Photofrin is an FDA-approved agent for PDT of cancers of esophagus, lung and skin (11). Several other dyes are currently under different phases of clinical studies for various cancers (12).

However, in regard to breast cancer, PDT has so far been used only in recurrent cases, with moderate success (13–17). It was observed that, although tumor nodules in the focal area could be controlled by PDT, new lesions appeared outside the area of treatment (17). It is likely that non-specific distribution of the PDT dye leads to only partial cytotoxicity and resultant cell-death. Thus, new methods of exploiting PDT to effectively combat a wide variety of cancers, especially breast cancer, would be particularly welcome.

SUMMARY OF THE INVENTION

The invention is directed to compositions and methods for their use to treat a patient suffering from a cancer of a cell type in which the estrogen receptor is expressed, e.g., breast, ovarian or endometrial cancer, by the selective delivery of PDT dyes to the tumor cells of the patient. The active compounds in the compositions of the invention are conjugates consisting of an estrogen or anti-estrogen portion, a tether or linker portion and a porphyrin portion. The method of the invention exploits an active process that involves strong and specific interaction between a nuclear receptor and its cognate ligand. A representative ligand (delivery vehicle), e.g., estradiol, is chemically coupled to a PDT dye (toxin), e.g., a porphyrin, to target the cognate nuclear receptor (delivery address), e.g., estrogen receptor, expressed in malignant cells. Administration of this conjugate to the patient results in the selective delivery of the conjugate and the toxin to the patient's cancer cells. Once the dye is localized selectively in the tumor, it is later activated to the cytotoxic state by exposure of the tumor to light of a suitable wavelength.

In particular, the conjugates of the invention have the structure:

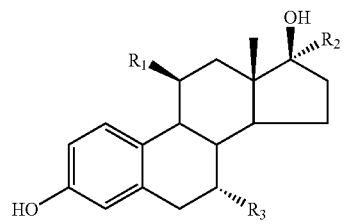

wherein
$R_1$=X—Y—$(CH_2)_n$—X—Y—P, where X=O, NH, S; Y=C(=O), C(=S), n=1–20, $R_2,R_3$=H; or
$R_1$=X—Y—$(CH_2)_n$—Y—X—P, where X=O, NH, S; Y=C(=O), C(=S), n=1–20, $R_2,R_3$=H; or
$R_1$=Z-$(CH_2)_n$—X—Y—P, where X=O, NH, S; Y=C(=O), C(=S); Z=C≡C, C=CH, $CH_2$—$CH_2$, n=1–20, $R_2,R_3$=H; or
$R_2$=X—Y—$(CH_2)_n$—X—Y—P, where X=O, NH, S; Y=C(=O), C(=S), n=1–20, $R_1,R_3$=H; or
$R_2$=X—Y—$(CH_2)_n$—Y—X—P, where X=O, NH, S; Y=(=O), C(=S), n=1–20, $R_1,R_3$=H; or $R_2$=Z-$(CH_2)_n$—X—Y—P, where X=O, NH, S; Y=C(=O), C(=S); Z=C≡C, C=CH, $CH_2$—$CH_2$, n=1–20, $R_1$,$R_3$=H; or $R_3$=X—Y—$(CH_2)_n$—X—Y—P, where X=O, NH, S; Y=C(=O), C(=S), n=1–20, $R_1$,$R_2$=H; or $R_3$=X—Y—$(CH_2)_n$—Y—X—P, where X=O, NH, S; Y=C(=O), C(=S), n=1–20, $R_1$,$R_2$=H; or $R_3$=Z-$(CH_2)_n$—X—Y—P, where X=O, NH, S; Y=(=O), C(=S); Z=C≡C, C=CH, $CH_2$—$CH_2$, n=1–20, $R_1$,$R_2$=H;

or the structure:

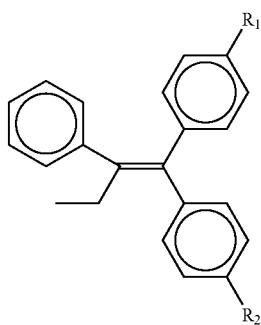

wherein $R_1$=O—$(CH_2)_2$—N$(CH_3)_2$, $R_2$=X—Y—$(CH_2)_n$—X—Y—P, where X=O, NH, S; Y=$CH_2$, C(=O), C(=S), n=1–20; or $R_1$=O—$(CH_2)_2$—N$(CH_3)_2$, $R_2$=X—Y—$(CH_2)_n$—Y—X—P, where X=O, NH, S; Y=C(=O), C(=S), n=1–20; or $R_1$=O—$(CH_2)_2$—N$(CH_3)_2$, $R_2$=Z-$(CH_2)_n$—X—Y—P, where X=O, NH, S; Y=C(=O), C(=S); Z=C≡C, C=CH, $CH_2$—$CH_2$, n=1–20; or $R_1$=X—Y—$(CH_2)_n$—X—Y—P, where X=O, NH, S; Y=$CH_2$, C(=O), C(=S), n=1–20, $R_2$=H, OH; or $R_1$=X—Y—$(CH_2)_n$—Y—X—P, where X=O, NH, S; Y=C(=O), C(=S), n=1–20, $R_2$=H, OH; or $R_1$=Z—$(CH_2)_n$—X—Y—P, where X=O, NH, S; Y=(=O), C(=S); Z=C≡C, C=CH, $CH_2$—$CH_2$, n=1–20, $R_2$=H, OH; or $R_1$=O—$(CH_2)_2$—N$(CH_2$—W$)CH_3$, where W=X—Y—$(CH_2)_n$—X—Y—P, where X=O, NH, S; Y=$CH_2$, C(=O), C(=S), n=1–20, $R_2$=H, OH; or $R_1$=O—$(CH_2)_2$—N$(CH_2$—W$)CH_3$, where W=X—Y—$(CH_2)_n$—X—Y—P, where X=O, NH, S; Y=$CH_2$, C(=O), C(=S), n=1–20, $R_2$=H, OH; or $R_1$=O—$(CH_2)_2$—N$(CH_2$—W$)CH_3$, where W=Z-$(CH_2)_n$—X—Y—P, where X=O, NH, S; Y=C(=O), C(=S); Z=C≡C, C=CH, $CH_2$—$CH_2$, n=1–20, $R_2$=H, OH, and wherein, for either structure, P=a natural or synthetic porphyrin derivative.

Particularly preferred conjugates according to the invention include:

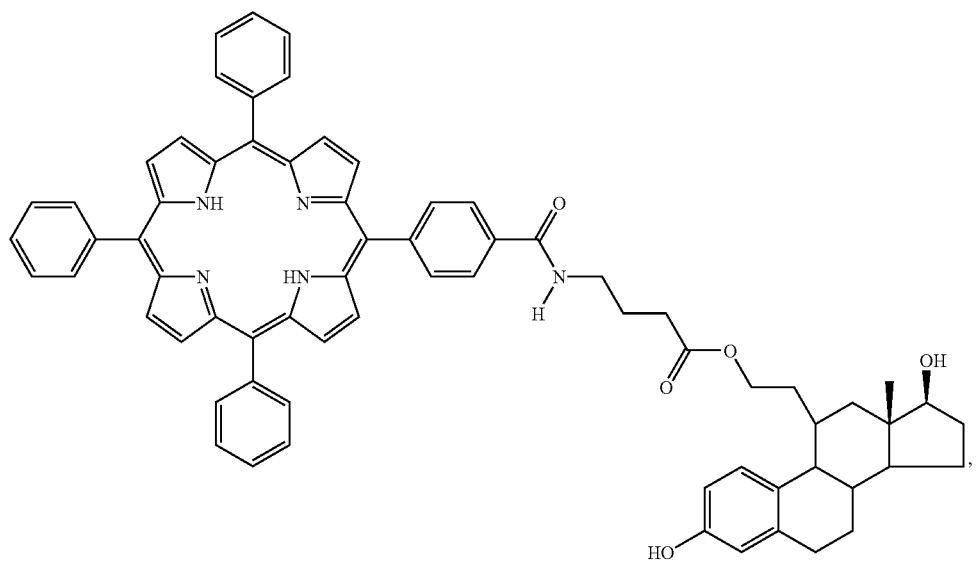

-continued

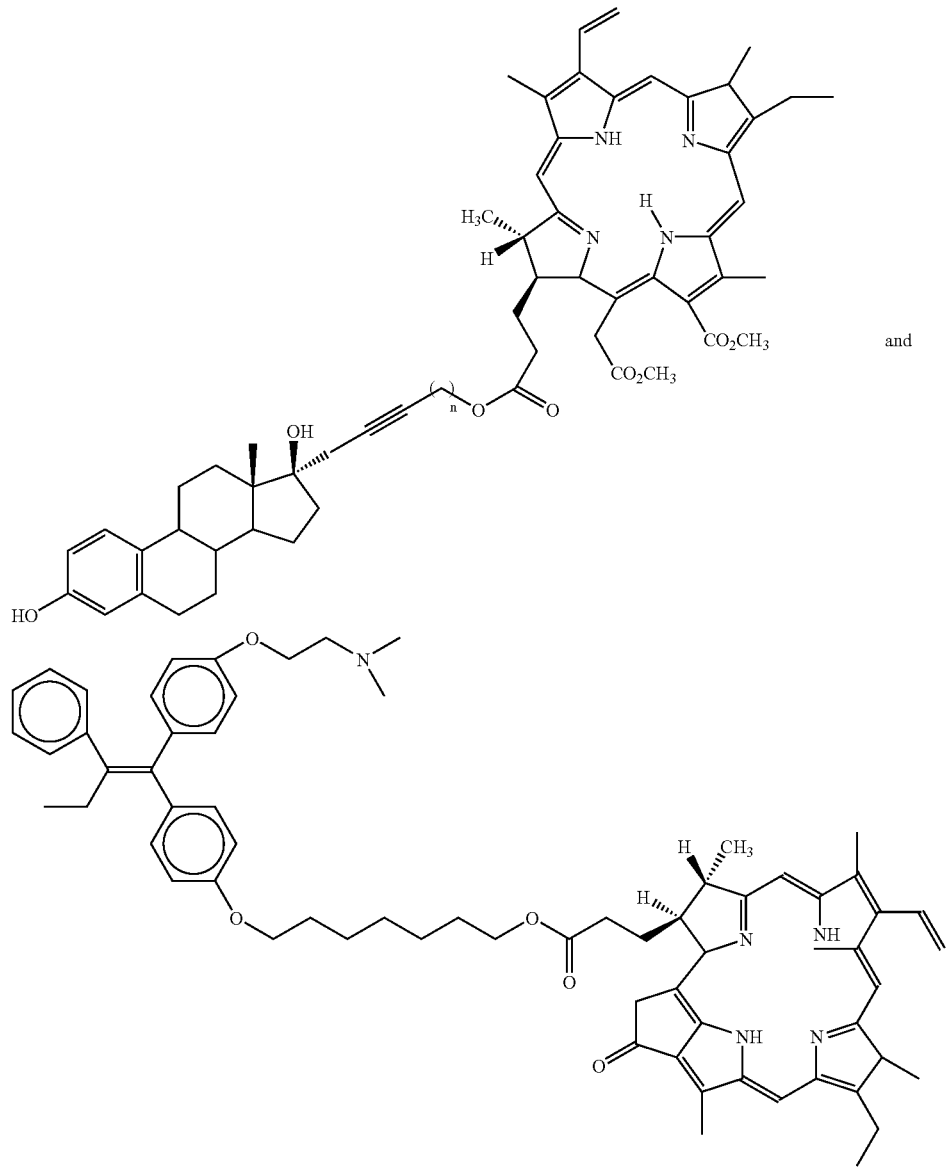

and

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 11 shows the general structures of conjugates according to the invention.

DETAILED DESCRIPTION OF THE INVENTION

The desired selective delivery of PDT dyes to tumor cells has been achieved using the compositions and methods of the invention by exploiting an active process that involves strong and specific interaction between a nuclear receptor and its cognate ligand. Nuclear receptors constitute a superfamily of proteins that are present in the nucleus of target cells. Estrogen receptor (ER), progesterone receptor (PR), retinoic acid receptor (RAR), retinoid receptor (RXR), glucocorticoid receptor (GR) and vitamin D receptor (VDR) are representative examples of these nuclear proteins. The most important property of nuclear receptors relates to their strong and specific interaction with their cognate ligands, e.g., estrogen (for ER), progesterone (for PR), vitamin D (for VDR), etc. It is known that the interaction between a nuclear receptor and its ligand results in the accumulation of the ligand into the nucleus of the target cell.

We hypothesized that a ligand (delivery vehicle) can be chemically coupled to a PDT dye (toxin) to target the cognate nuclear receptor (delivery address) expressed in malignant cells. This would result in the selective delivery of the conjugate and the toxin to cancer cells. Once the dye is localized selectively in the tumor, it can later be activated to the cytotoxic state by exposure of the tumor to light of a suitable wavelength.

Malignant cells often over-express the cognate nuclear receptors for steroid hormones. Therefore, the ligand portion of the above-mentioned conjugate will tend to localize into the nucleus of the tumor cell due to the strong and high-affinity interaction between the ligand and its cognate nuclear receptor. This process is enhanced by the natural tendency of the PDT dyes to accumulate into malignant cells. The resultant process ultimately will enhance the selectivity of accumulation of the PDT dye into malignant tissues and effectively lower the amount of the dye required for efficient and selective killing of malignant cells, with less toxicity and undesired side effects.

The nuclear ER is of particular interest in relation to cancer therapy since it is expressed in many breast, ovarian and endometrial cancer cells. Estradiol (estrogen) is the female sex hormone that interacts specifically with the nuclear ER. Therefore, to test this hypothesis, we chose estrogen-ER as the interacting system, breast cancer cells (the majority of which express ER) as the model target and estrogen/anti-estrogen-porphyrin conjugates as the model therapeutic agents.

The following examples are presented to illustrate the advantages of the present invention and to assist one of ordinary skill in making and using the same. These examples are not intended in any way otherwise to limit the scope of the disclosure.

Figure 1:
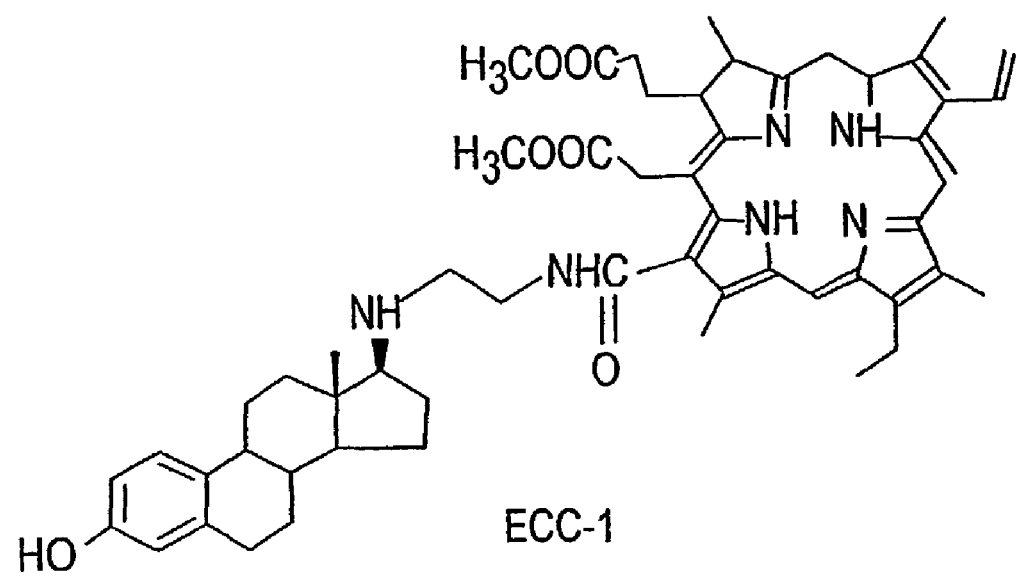
FIG. 1 shows the structures of two estragen-porphyrin conjugates tested in the development of the method of the invention.
Figure 1:
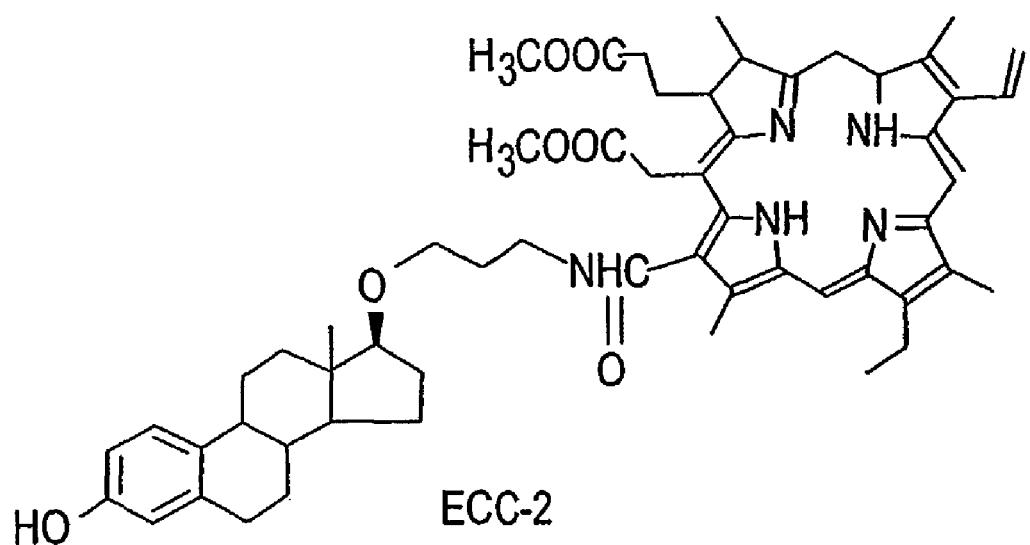

In our first attempt to develop therapeutic estrogen-porphyrin conjugates, we synthesized two compounds, ECC-1 and ECC-2 as shown in FIG. 1, in which chlorin e6-dimethyl ester, a porphyrin, is attached to estradiol via a C17-amino (ECC-1) or a C17-ether (ECC-2) group at the C17-OH position. ER-binding assays of ECC-1 and ECC-2 showed that the $K_i$ of ECC-2 was 100,000-fold less than that of estradiol and that ECC-1 had no significant binding.

PDT studies of ECC-2 vs. chlorin e6-dimethyl ester (the unconjugated porphyrin as control) were then carried out in ovarian and breast cancer cell lines (OVCAR-3 and MCF-7 cells respectively) to determine selective cellular uptake. The results of these assays indicated that there was no difference between chlorin e6 (the unconjugated porphyrin) and ECC-2 in PDT studies at every concentration tested. These results thus suggested that if the ER is to be an effective target for cancer therapy, good ER-binding by the estrogen-porphyrin conjugate is required.

Figure 2:
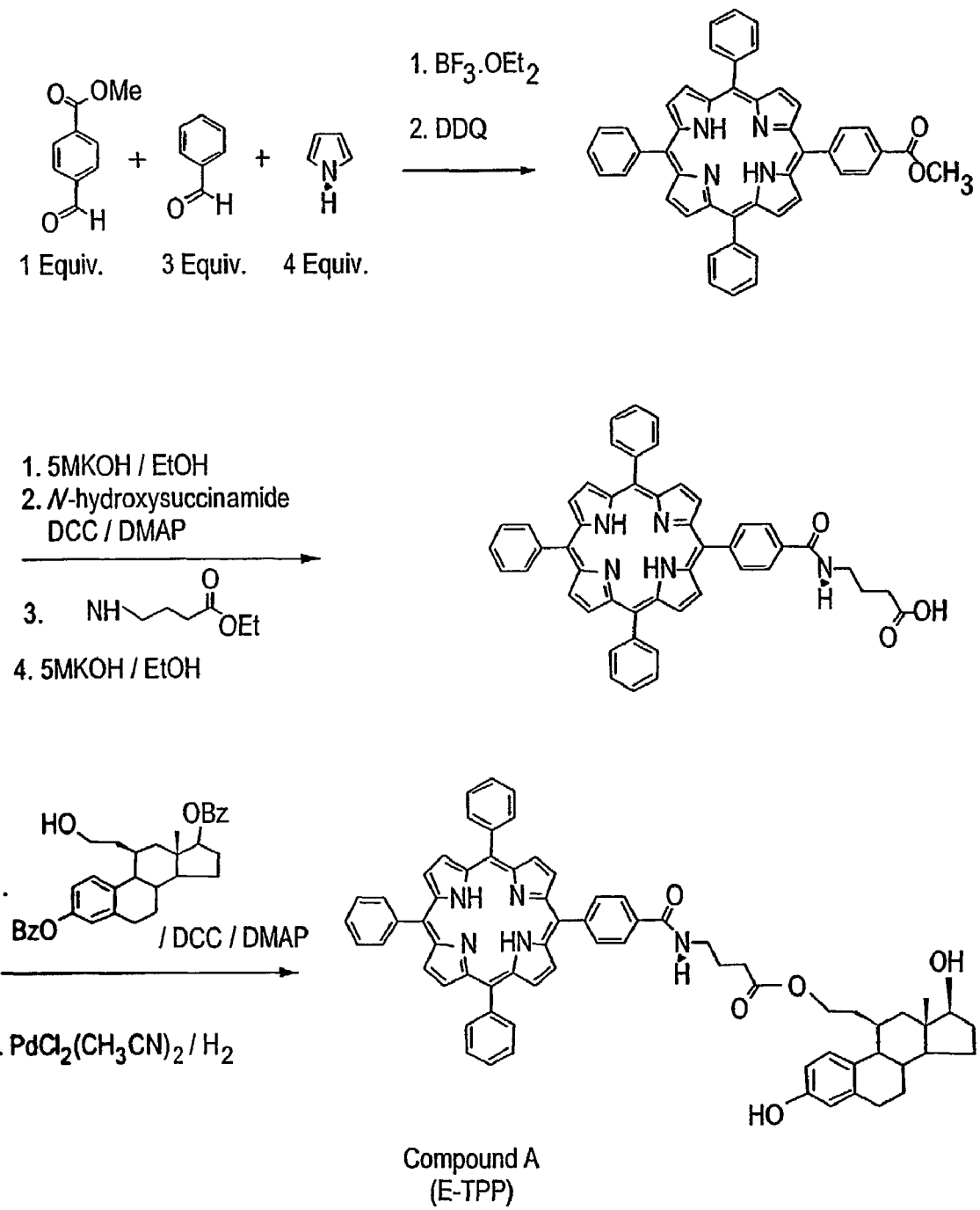
FIG. 2 shows the synthesis of a C11-β-modified estradiol-tetraporphyrin conjugate according to the invention.

For our next series of candidate compounds, we modified the C11-β position of estradiol. 11β-(2-Hydroxy)ethylestradiol, a known compound (18), was coupled to a tetraphenyl porphyrin derivative to produce a $C_{11}$-β-estradiol-porphyrin conjugate in which the porphyrin moiety is attached to estradiol via a nine atom tether. Our synthetic scheme for the conjugate, as shown in FIG. 2, involves a dicyclohexylcarbodiimide (DCC)-coupling between 11β-(2-hydroxy)ethyl, 3,17-dibenzyl estradiol and a tetraphenyl porphyrin derivative containing a six atom tether and a carboxylic acid group. Removal of the benzyl protecting groups produced the desired conjugate (Compound A, E-TPP) between estradiol and porphyrin via a nine atom tether.

The ER-binding properties of the conjugate (E-TPP) were assessed by competitive binding assays using standard procedures. For example, 2 nM of baculovirus-expressed recombinant ER (PanVera, Madison, Wis.) was incubated with 0.125 nM of [$^3$H]17β-estradiol in the presence of increasing concentrations of estradiol or E-TPP in an assay buffer (10 mM Tris, pH 7.5, 10% glycerol, 2 mM of monothioglycerol and 1 mg/ml BSA) for 15 h at 4° C. After the incubation period, a 50% hydroxylapatite (HAP) slurry was added to remove unbound [$^3$H]17β-estradiol from ER-bound [$^3$H]17β-estradiol. The mixture was centrifuged and the pellet was washed three times with the wash buffer (40 mM Tris, pH 7.4, 100 mM KCl, 1 mM EDTA, 1 mM EGTA). The HAP pellet was re-suspended in 200 μl ethanol and scintillation cocktail. The amount of radioactivity in each sample was determined in a liquid scintillation counter.

Figure 3:
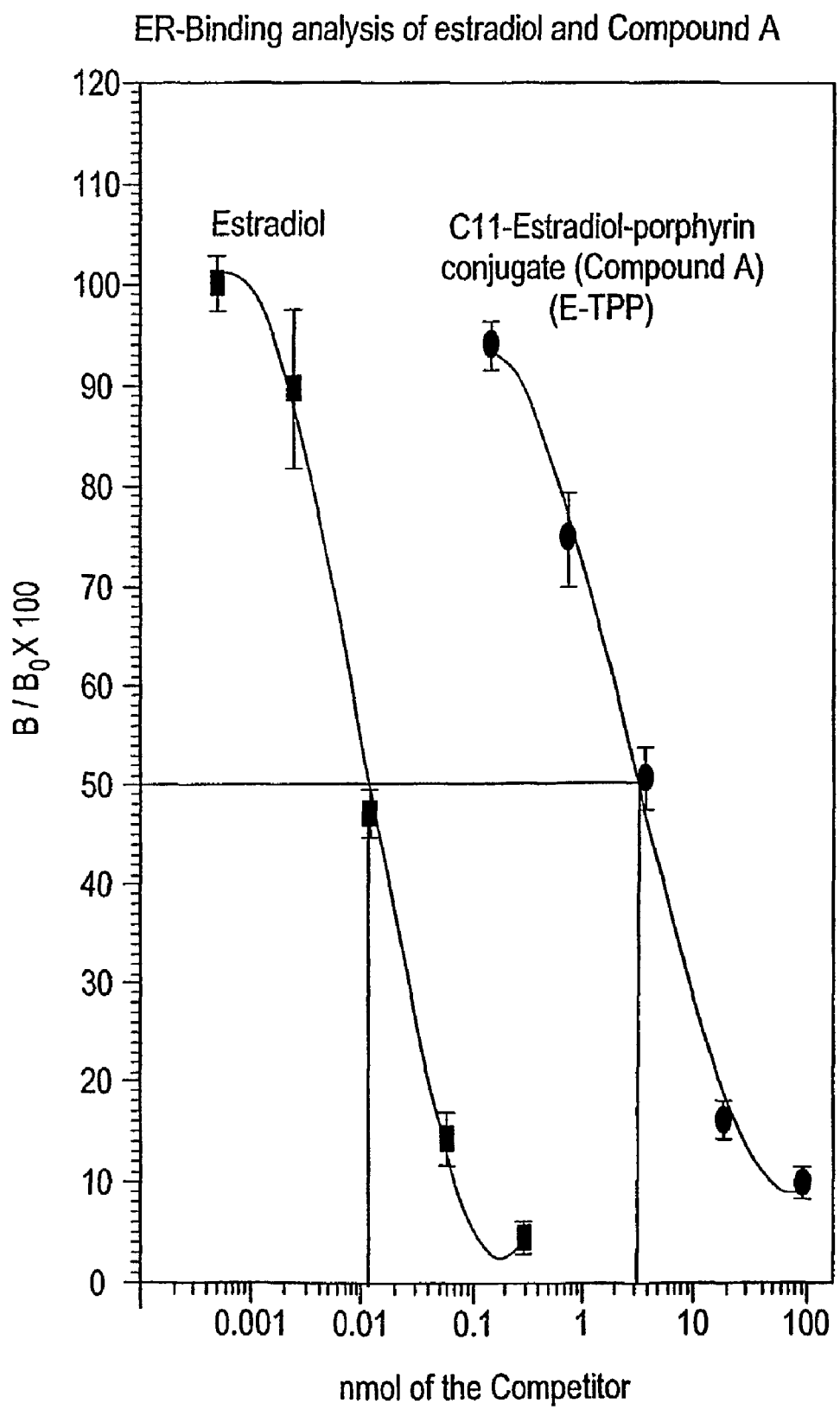
FIG. 3 shows competitive binding assays of the C11-β-modified estradiol-tetraporphyrin conjugate of FIG. 2 and estradiol with recombinant ER.

The results of these assays, shown in FIG. 3, indicate that E-TPP bound specifically to the ER with an $EC_{50}$ of 3.2 nmol compared with 0.012 nmol for estradiol. This result is not surprising because modification of a natural molecule (e.g., estradiol) usually leads to a decreased binding affinity for its receptor. However, the extent of such a decrease is unpredictable.

After the extent of binding of E-TPP to ER was established, the differential uptake of this conjugate compared to the parent porphyrin was studied in two human breast cancer cell lines, MCF-7 containing ER (ER +ve) and Hs578t without ER (ER −ve). MCF-7 and Hs578t cells (100,000/well in a 24 well plate) were grown in DMEM (Dulbeco's modified Eagle medium) containing 5% charcoal-stripped fetal bovine serum (FBS) in the absence of phenol red. The cells were serum-depleted for one day, and then treated with 0.5 of media containing increasing concentrations of unconjugated dye (TPP) or the conjugate (E-TPP) (2.5, 5, 10, 20 and 40 μM). The cells were treated with dihydrofluorescene diacetae (2 mM final concentration) in 0.5 ml of DMEM without phenol red for 30 minutes in the incubator. The wells were washed 3 times with ice cold PBS, and cells were dissociated from the plate using enzyme free cell dissociation solution (Speciality Media, Lavallette, N.J.). The plates were exposed to red light using an overhead projector for 20 minutes at 25° C. (to photoactivate the porphyrin in order to generate a reactive oxygen species, which oxidizes the non-fluorescent, reduced fluorescene derivative to convert it to a fluorescent molecule). The cells were lysed by the addition, twice, of 0.5 ml PBS containing 0.4% Triton X100 to each well followed by pipetting the contents of each well up and down 3 times to complete the lysis step. The contents of each well were transferred to individual microcentrifuge tubes and centrifuged for 5 minutes. The fluorescence was measured at 530 nm with excitation at 485 nm.

Figure 4:
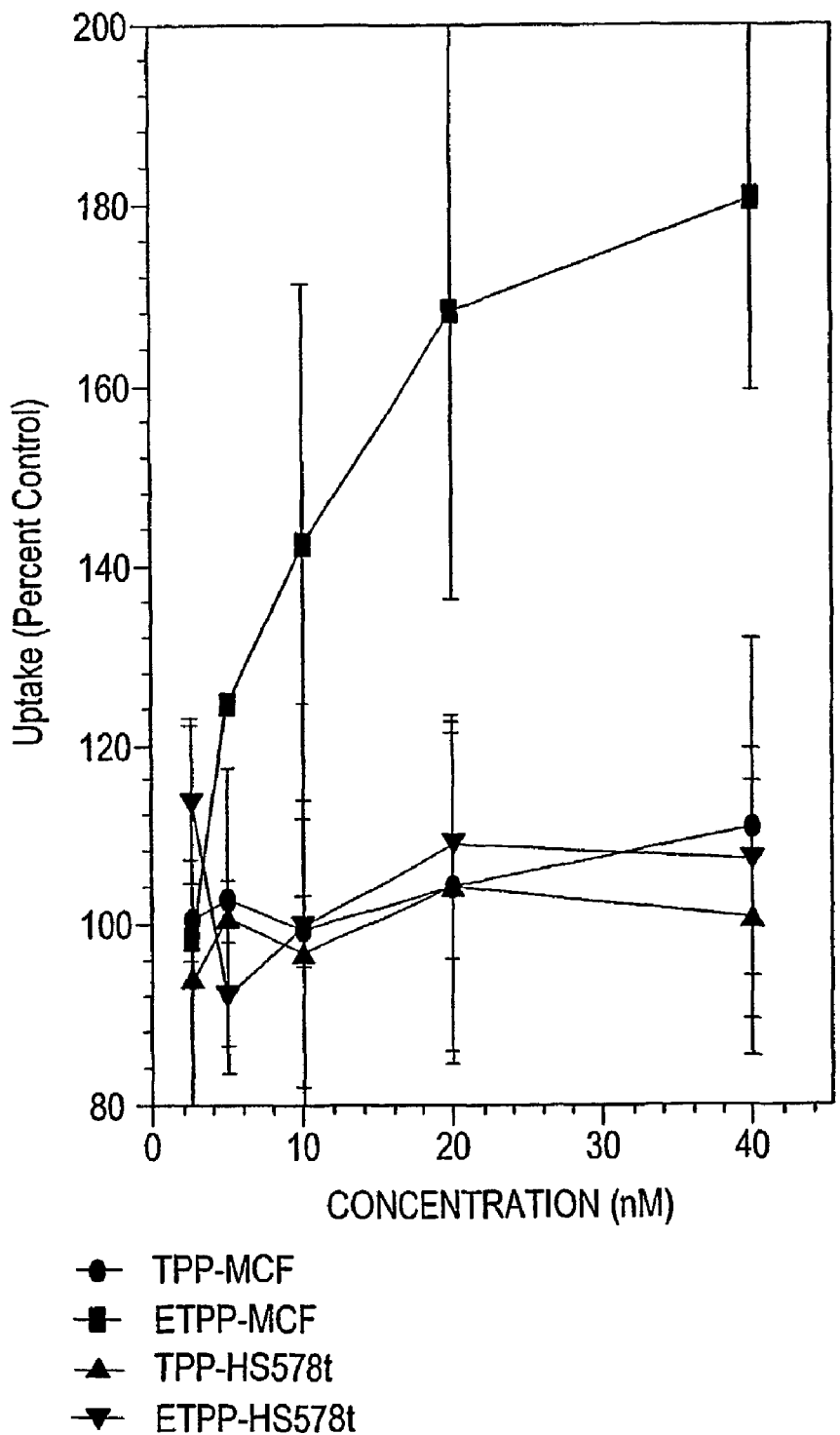
FIG. 4 shows cellular uptake assays of unconjugated porphyrin dye (TPP) and the estradiol-porphyrin conjugate of FIG. 2 (ETPP) with ER-positive, MCF-7, and ER-negative, HS578t, cells.

Referring to FIG. 4, it can be seen that the uptake of the unconjugated dye (TPP) was substantially lower than that of the conjugate (E-TPP) in both ER +ve MCF-7 and ER −ve Hs578t cells. However, for the conjugate (E-TPP), uptake was significantly higher and concentration-dependent only in the case of ER +ve MCF-7 cells. MCF-7 and Hs578t are both human breast cancer cells, but the former contains ER and the later does not. Therefore, the above results strongly supported the first part of our hypothesis that the uptake/accumulation of the PDT dye (by hormone-sensitive breast cancer cells) can be significantly enhanced by targeting nuclear ER with estrogen-dye conjugates, as long as the estradiol delivery molecule retains a sufficient level of ER binding capability.

In the next study, we determined the cell-killing properties of E-TPP and observed that neither the conjugate (E-TPP) nor the unconjugated dye (TPP) was very effective in killing cells (MCF-7 and Hs578t). Upon searching the literature, we noted that tetraphenylporphyrin and its derivatives have a low efficiency in killing cells upon exposure to light of the appropriate wavelength (one that is absorbed by the porphyrin ring structure). Therefore, we must choose a porphyrin for our conjugate that can be shown to be capable, independently, of killing cells in culture.

Figure 5A:
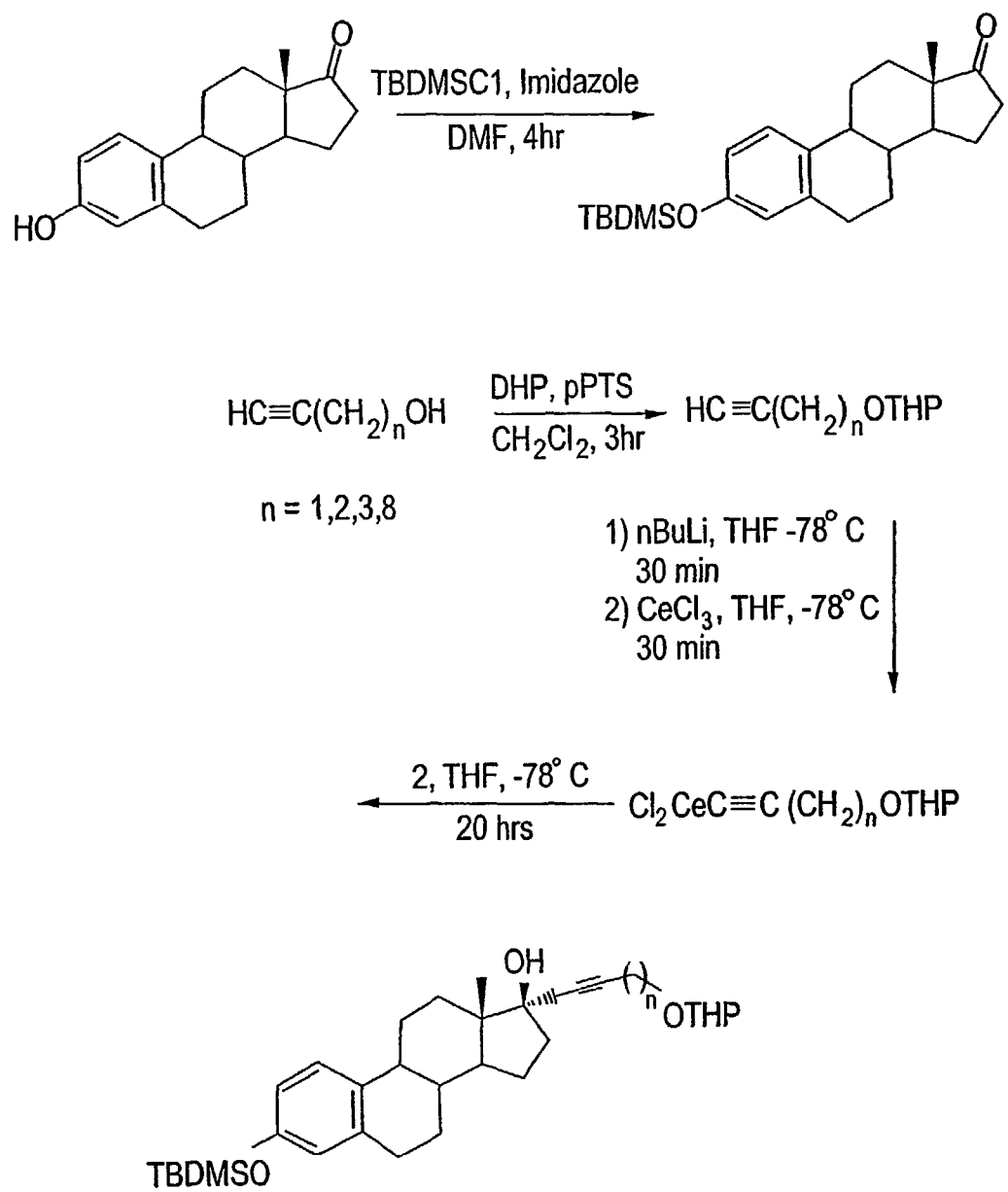
FIGS. 5a and 5b show a scheme for the synthesis of C17-α-ethynyl-porphyrin conjugates according to the invention (Compounds B–E)
Figure 5B:
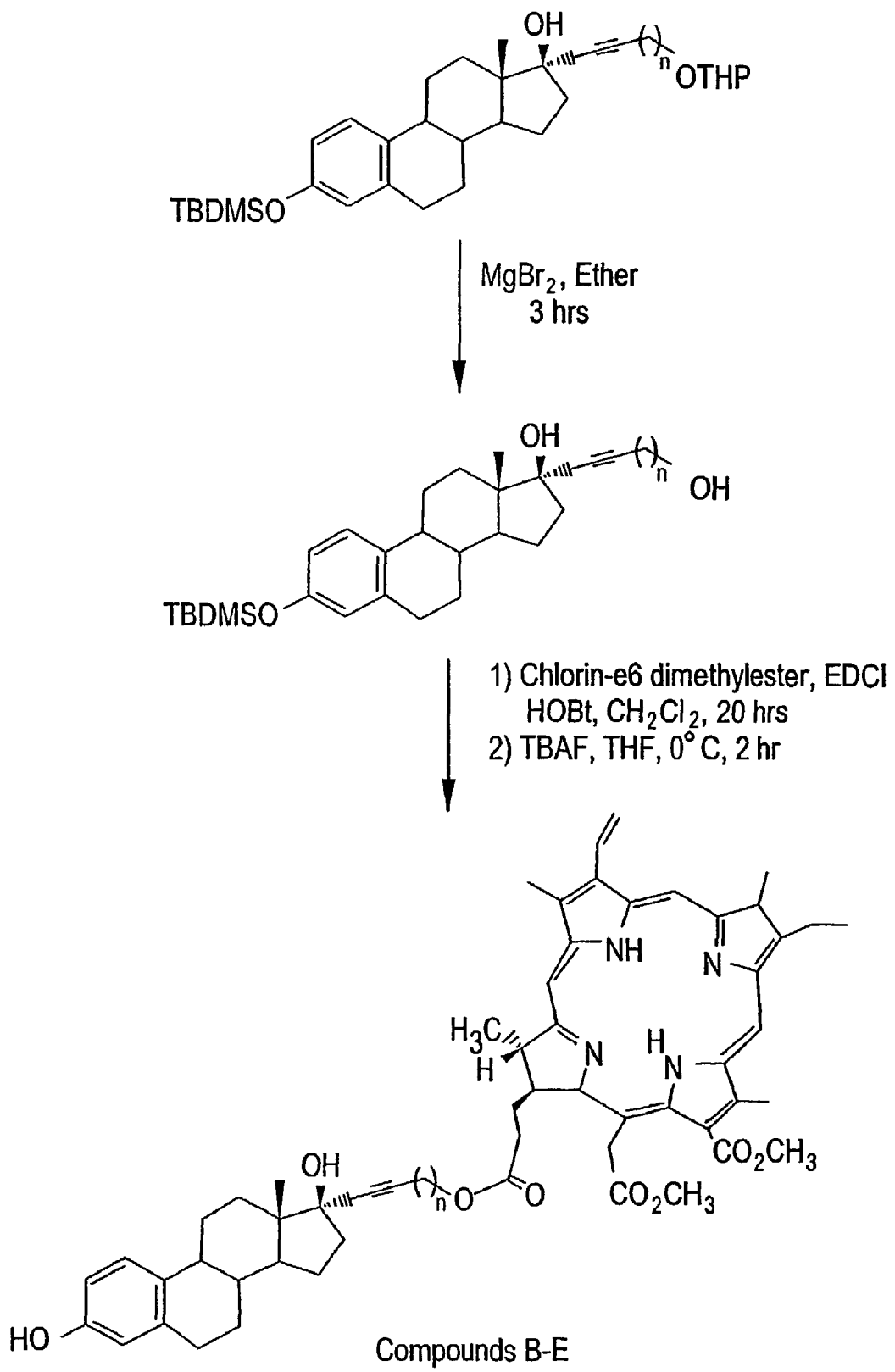

For the next set of conjugates, we attached chlorin e6-dimethyl ester, a porphyrin derivative, to 17α-ethynyl derivatives of estradiol. Chlorin e6 is known to be an efficient PDT dye (19), while 17α-ethynyl estradiol derivatives are known to possess strong ER-binding (20). As shown in the synthetic scheme presented in FIGS. 5a–5b, chlorin e6-dimethyl ester was attached to the 17α-ethynyl derivatives of estradiol via tethers of various lengths, both to test the activity of a conjugate containing an active porphyrin compound as well as an estradiol derivative with minimum retained ER binding capability and to study the effects of tether length on ER-binding. Synthesis of these compounds (Compound B–E) included nucleophilic addition of the tetrahydropyranyl (THP)-protected lithiated alkynyl derivatives to tert.butyldimethylsilyl (TBDMS) protected estrone, followed by selective deprotection of the alcohol and coupling to chlorin e6-dimethyl ester. Deprotection of the TBDMS-ether produced the desired compounds (Compound B, n=1, Compound C, n=2, Compound D, n=3, Compound E, n=8). The four atoms in the tether contributed by the propionic acid side chain come from the porphyrin and are common to all compounds.

Figure 6:
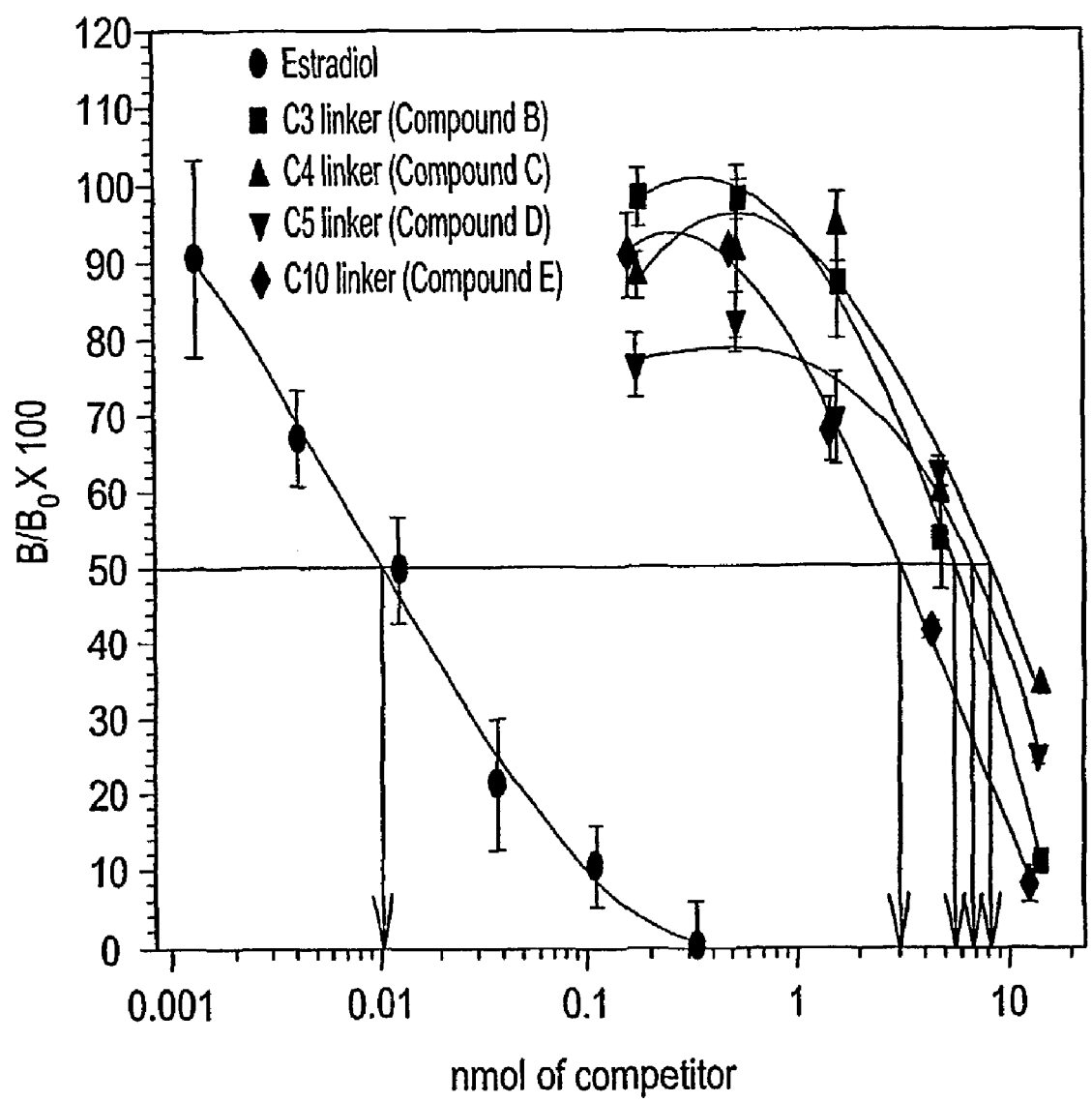
FIG. 6 shows the results of a binding analysis of estradiol and Compounds B–E with recombinant ER.

Competitive ER-binding assays of Compounds B–E were carried out as described earlier. The results of these assays, as shown in FIG. 6, demonstrated that all the compounds possessed specific binding for ER ($EC_{50}$ for Compounds B–E were 5.5, 8, 6.5 and 3 nmol, respectively, compared with 0.01 nmol for estradiol). It is noteworthy that there was no substantial advantage in increasing the tether length towards ER-binding.

Once the ER-binding properties of Compounds B–E were established, we determined the light-induced cell-killing properties of Compounds B and C in MCF-7 cells. Specifically, MCF-7 cells were grown as described earlier and treated with the Compounds B and C at a final concentration of 5 µg/ml or 10 µg/ml for 60 minutes in 0.5 ml of DMEM. As a control, one set of wells was treated with DMEM alone. The experiments were carried out in two sets, one for exposure to light and one as a dark control, to determine the inherent toxicity of the test compounds in the absence of light. At the end of 60 minutes, one plate was exposed to red light from a light box, as described earlier, for 60 minutes. The media containing the test compounds in both the plates were replaced with DMEM containing 5% FBS and 1% Penn Strep and cells were allowed to grow for 16 hours. The viability of the cells after PDT treatment was determined by using a methylene blue assay procedure. Briefly, the plates were cooled on ice and the wells were washed twice with 0.5 ml of ice cold PBS. Methanol (chilled at −20° C.) was added to each well (0.5 ml/well) and incubated on ice for 20 minutes. Methanol was removed by suction and the plates were air dried for 20 minutes. Treatment with chilled methanol was carried out to fix the cells. Methylene blue solution (1% solution in 10 mM Borate buffer, pH 8.5) was added to each well (0.25 ml/well) and the samples were incubated on ice for 30 minutes. The plates were washed 4 times with 10 mM borate buffer, pH 8.5, and the bound dye was eluted by the addition of 1.0 ml of methylene blue elution solution (ethanol:0.1M HCL, 1:1). The color intensity was determined spectrophotometrically at 650 nm. The viable cells were expressed as percent control (control being untreated cells).

Figure 7:
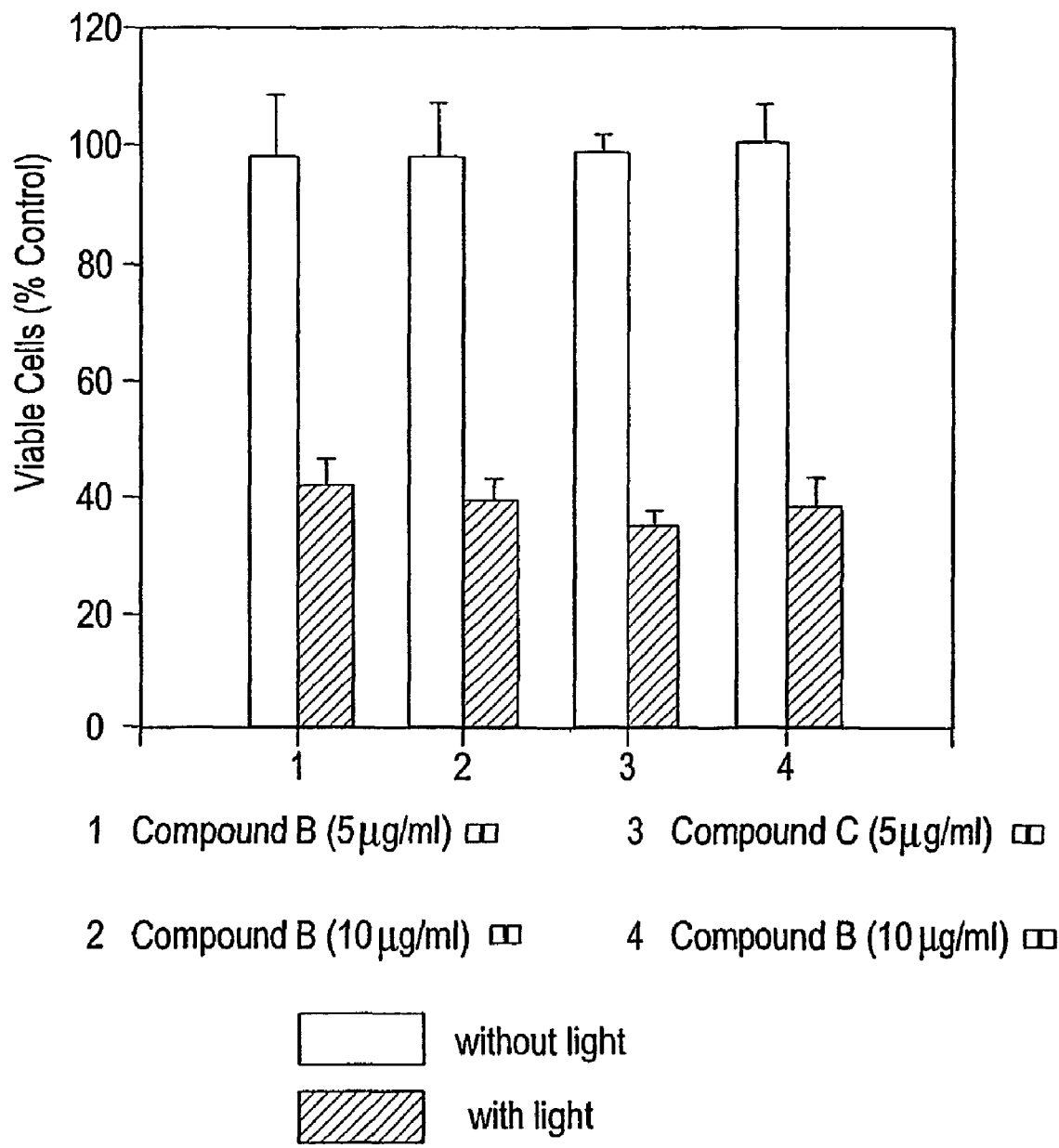
FIG. 7 shows the results of treatment of MCF-7 breast cancer cells with Compounds B and C.

As shown in FIG. 7, Compounds B and C at both 5 µg/ml and 10 µg/ml reduced the viable cell-count to approximately 40% upon exposure of the treated cells to red light (solid bars). In contrast, there was no discernible toxicity when the cells were not exposed to light (clear bars). Collectively, the above results show that it is possible to selectively deliver certain porphyrins (e.g., chlorin e6-dimethyl ester) to breast cancer cells as conjugates of estrogen and to kill the tumor by activation of the cytotoxic properties of the porphyrin. As discussed earlier, such a selective accumulation leads to a reduced requirement for PDT dye compared to traditional PDT and, therefore, to a decrease in unwelcome side effects.

Figure 8:
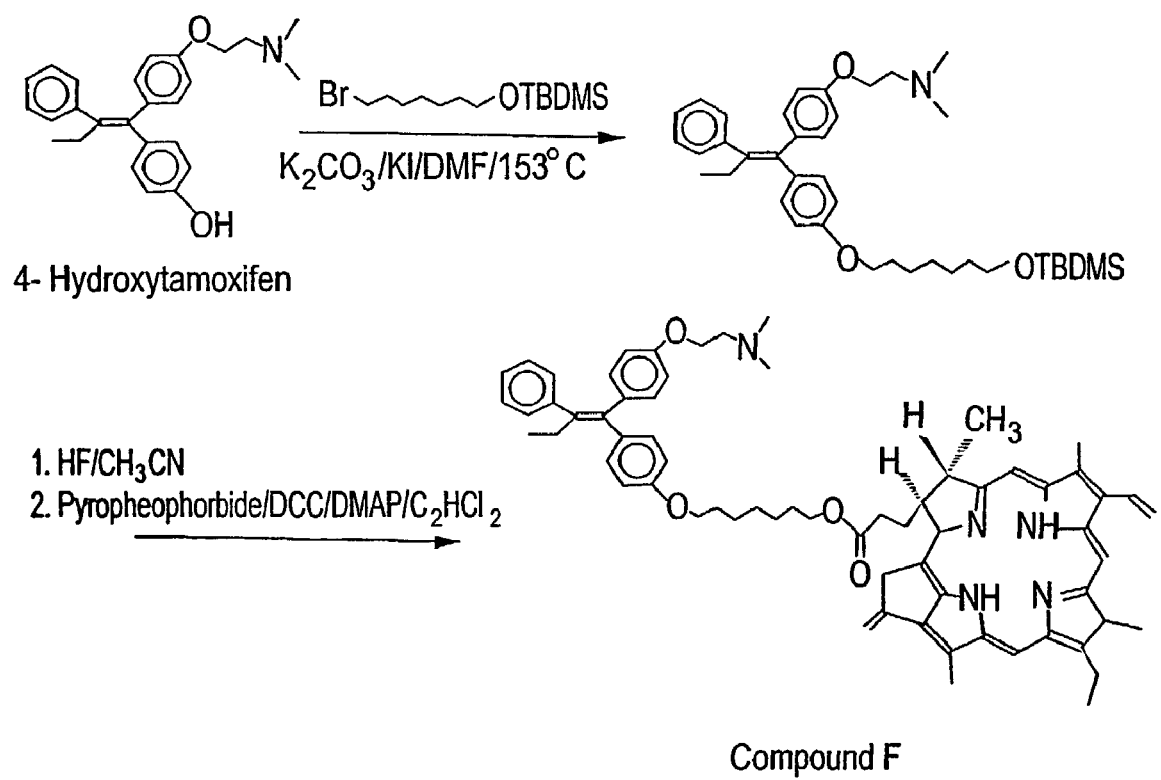
FIG. 8 shows a scheme for the preparation of a conjugate according to the invention comprising a complex of a porphyrin with 4-hydroxytamoxifen (Compound F)

For another series of candidate compounds, we examined the properties of 4-hydroxytamoxifen (4-OH-TAM), a metabolite of tamoxifen, which is an anti-estrogen and binds strongly to the ER. First, we chemically attached a seven atom tether to this compound via the phenolic hydroxyl group at the 4-position. Removal of the tert.butyldimethylsilyl (TBDMS) protecting group from the alcohol and DCC-coupling with pyropheophorbide (Frontier Scientific, Logan, Utah) provided the tamoxifen-porphyrin conjugate (Compound F), as shown in FIG. 8.

Figure 9:
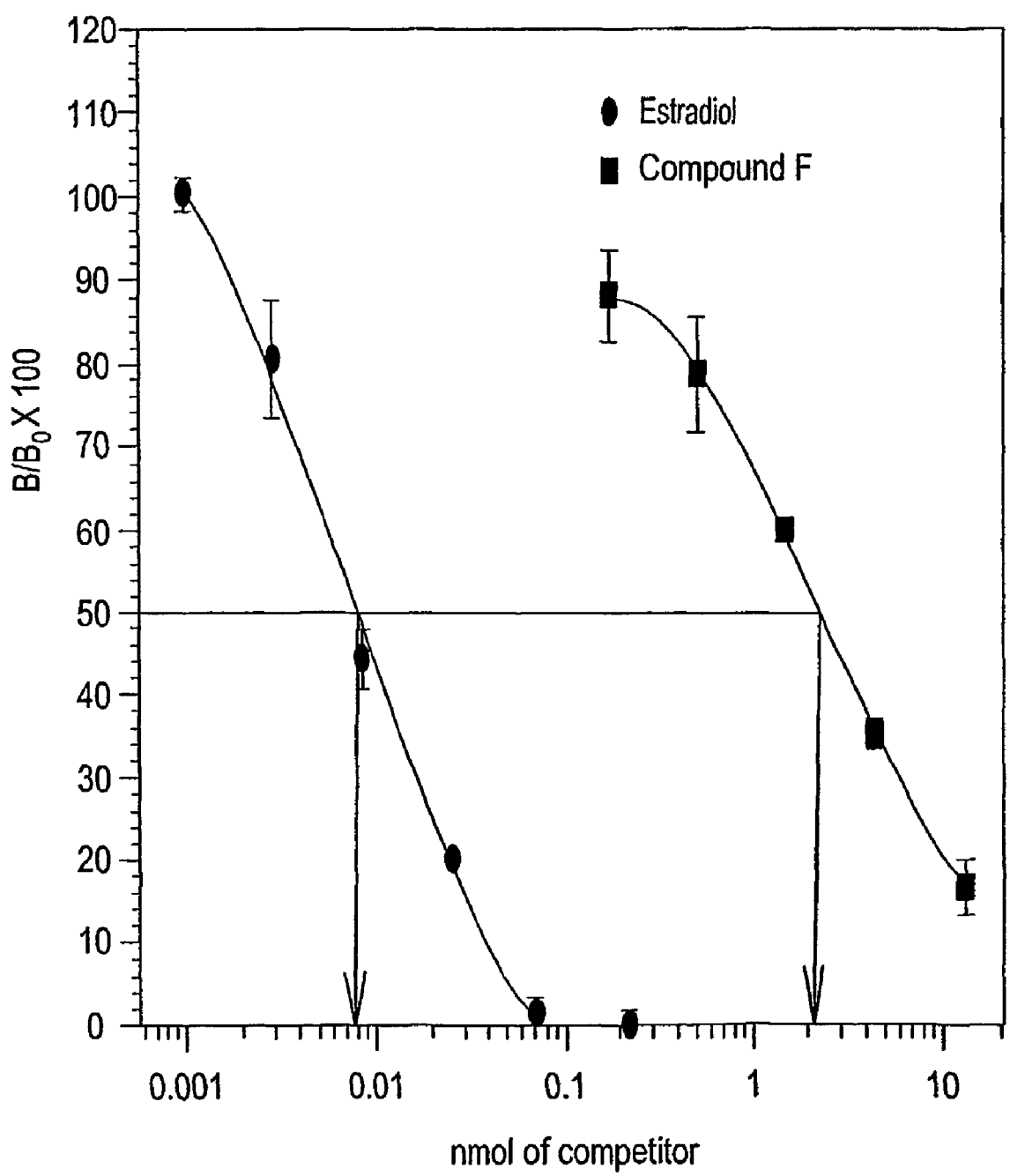
FIG. 9 shows the results of a binding analysis of estradiol and Compound E with recombinant ER.

Competitive binding assays of Compound F with ER were carried out as described earlier. The results of these assays, as given in FIG. 9, showed that Compound F possessed specific binding for ER ($EC_{50}$ for Compound F was 2.2 nmol compared with 0.008 nmol for estradiol).

Figure 10:
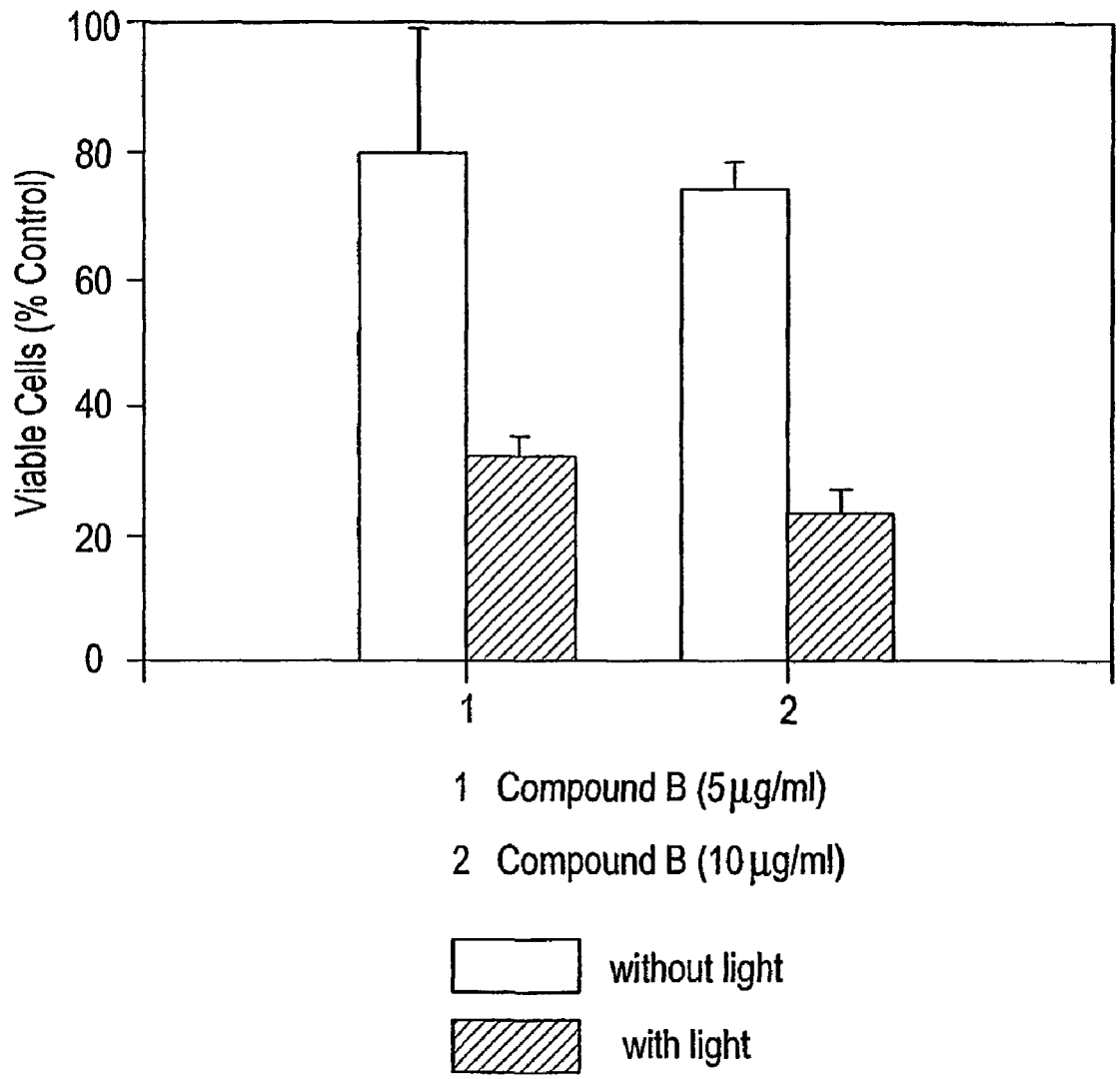
FIG. 10 shows the results of treatment of MCF-7 breast cancer cells with Compound F.

Once the binding characteristics of the tamoxifen-porphyrinconjugate (Compound F) to ER were established, we carried out a light-induced cell-killing study (similar to that carried out with Compounds B and C) with MCF-7 breast cancer cells. The results of these assays, given in FIG. 10, showed that the viable cell count for cells treated with Compound F and exposed to light was significantly lower than that for cells kept in the dark, thus demonstrating the value of Compound F as a candidate for PDT treatment.

Use

In the method of the invention, an estrogen/anti-estrogen-porphyrin conjugate of the invention is administered to a patient suffering from a cancer of a cell type in which the estrogen receptor is expressed, e.g., breast, ovarian or endometrial cancer, as a therapeutic composition in pharmaceutically acceptable inert carrier substances, e.g., physiological saline. The therapeutic compositions may be administered orally, topically, or parenterally, (e.g., intranasally, subcutaneously, intramuscularly, intravenously, or intraarterially) by routine methods. For example, the therapeutic compositions of the invention may be administered in a sustained release formulation using a biodegradable biocompatible polymer, or by on-site delivery using micelles, gels or liposomes. The conjugates of the invention can be administered in a dosage, e.g., of 50 µg/kg/day to 25 mg/kg/day. Optimal dosage and modes of administration can readily be determined by conventional protocols. The therapeutic compositions of the invention can be administered independently or co-administered with another antineoplastic agent. Preferably, the conjugate is administered intravenously in saline or in the form of liposomes of dipalmityl phosphatidyl choline at a dosage of from 0.25 mg/kg to 8.0 mg/kg over a period of 30 min, as generally described (21). The portion of the patient's body containing the tumor cells is subsequently exposed to red light, e.g., from a xenon arc laser, to activate the cytotoxic state of the porphyrin portion of the conjugate.

The conjugate of the invention consists of an estrogen/anti-estrogen portion, a tether or linker portion and a porphyrin portion. The estrogen/anti-estrogen portion is an analog of estradiol or tamoxifen, as shown in FIG. 11, with an attached tether or linker portion. The estrogen/anti-estrogen chosen to be incorporated in the conjugate of the invention preferably exhibits a $K_i$ in an ER-binding assay, as described herein, of not less than 1/1000 that of estradiol.

The porphyrin portion of the conjugate of the invention can be any porphyrin derivative, natural or synthetic, having the general cyclic tetrapyrrole core structure shown in FIG. 11. Numerous natural and synthetic modifications of the general cyclic tetrapyrrole structure of porphyrins have been known for decades. A large number of these compounds are also available commercially (e.g., Sigma-Aldrich, Milwaukee, Wis., Frontier Scientific, Logan, Utah). The porphyrin chosen to be incorporated in the conjugate can be tested for an ability to be toxic towards human cells in a test such as the following: MCF-7 cells are treated with various doses, e.g., according to the examples herein, of the test porphyrin or of chlorin e6-dimethyl ester (as the positive control) followed by exposure to red light. A second set of cells, treated with the test porphyrin or chlorin e6-dimethyl ester will be kept in the dark (negative control). Each set of cells will be tested for viable cell-count, also as described herein. Preferably, a porphyrin used in the conjugate of the invention has a cell-kill value of not less than 10% of that of chlorin e6-dimethyl ester.

REFERENCES

1. Thomas J. Dougherty, Charles J. Gomer, Barbara W. Henderson, Giulio Jori, David Kessel, Mladen Korbelik, Johan Moan, Qian Peng (1998) Journal of the National Cancer Institute 90: 889–905.
2. Pass, H. I. Photodynamic therapy in oncology: mechanisms and clinical use. (1993) J. Natl. Cancer Inst. 85: 443–456.
3. Dougherty, T. J. Photodynamic therapy (PDT) of malignant tumors. (1984) CRC Crit. Rev. Oncol./Hematol. 2: 83–116.
4. Bachor, R., Shea, C. R., Gillies, R., and Hasan, T. Photosensitized destruction of human bladder carcinoma cells treated with chlorin e6-conjugated microspheres. (1991) Proc. Natl. Acad. Sci. USA 88: 1580–1584.
5. Sery, T. W., Shields, J. A., Ausburger, J. J., et al. Photodynamic therapy of human ocular cancer. (1987) Surg. 18: 413–418.
6. Bruce, R. A., Jr., and MacCaughan, J. S., Lasers in uveal melanoma. (1989) Opthalm. Clin. N. Am. 2: 597.
7. Dougherty, T. J. Photosensitization of malignant tumors. (1986) Semin. Surg. Oncol. 2: 24–27.
8. McCaughan, J. S., Jr., Guy, J. T., Hicks, W. et al. Photodynamic therapy for cutaneous and subcutaneous malignant neoplasms.(1989) Arch. Surg. 124: 211–216.
9. Santoro, O., Bandieramonte, G., Melloni, E. et al. Photodynamic therapy by topical meso-tetraphenylporphine-sulfonate tetrasodium salt administration in superficial basal cell carcinoma. (1990) Cancer Res. 50: 4501–4503.
10. Wilson, B. W., Mang, T. S., Cooper, M. C. et a. Use of photodynamic therapy for the treatment of extensive basal cell carcinomas. (1990) Facial Plastic Surg. 6: 185–189.
11. Sanfilippo N J, Hsi A, DeNittis A S, Ginsberg G G, Kochman M L, Friedberg J S, Hahn S M. Toxicity of photodynamic therapy after combined external beam radiotherapy and intraluminal brachytherapy for carcinoma of the upper aerodigestive tract. (2001) Lasers Surg Med 28:278–281.
12. Granville D J, McManus B M, Hunt D W. Photodynamic therapy: shedding light on the biochemical pathways regulating porphyrin-mediated cell death. (2001) Histol Histopathol 16:309–317.
13. Kennedy, J.: In Photodynamic therapy for cancer at Kingston and Hamilton. In Porphyrin photosensitization (Kessel, D., Dougherty, T. J. eds.). New York: Plenum Press, 1983, p 53.
14. Koren, H., Alth, G., Schenk, G. M., and Jindra, R. H. Photodynamic therapy an alternative pathway in the treatment of recurrent breast cancer. (1994) Intl J. Radiation Oncol. 28: 463–466.
15. Khan, S. A., Dougherty, T. J., and Mang, T. S. An evaluation of photodynamic therapy in the management of cutaneous metastases of breast cancer. (1993) E. J. Cancer 29A: 1686–1690.
16. Aberzik, W. J., Silver, B., Henderson, I. C. et al. The use of radiotherapy for treatment of isolated locoregional recurrence of breast carcinoma after mastectomy. (1986) Cancer 58: 1214–1218.

17. Schuh, M., Nseyo, U. O., Potter, W. R. et al. Photodynamic therapy for palliation of locally recurrent breast cancer. (1987) J. Clin. Oncol. 5: 1766–1770.
18. Hanson R N, Napolitano E, Fiaschi R. Synthesis and evaluation of libeta-substituted 21-chloro/iodo-(17alpha, 20E/Z)-19-norpregna-1,3,5(10),20-tetraene-3, 17beta-diols: high-affinity ligands for the estrogen receptor. (1998) J Med Chem 41:4686–92.
19. Del Governatore M, Hamblin M R, Shea C R, Rizvi I, Molpus K G, Tanabe K K, Hasan T. Experimental photoimmunotherapy of hepatic metastases of colorectal cancer with a 17.1A chlorin(e6) immunoconjugate. (2000) Cancer Res 60):4200–4205.
20. Anstead, G. M., Carlson, K. E., and Katzenellenbogen, J. A. (1997) The estradiol pharmacophore: ligand structure-estrogen receptor binding affinity relationships and a model for receptor binding site. Steroids 62: 268–303.
21. Rosenthal M A, Kavar B, Hill J S, Morgan D J, Nation R L, Stylli S S, Basser R L, Uren S, Geldard H, Green M D, Kahl S B, Kaye A H. Phase I and pharmacokinetic study of photodynamic therapy for high-grade gliomas using a novel boronated porphyrin. (2001) J Clin Oncol. 19:519–524.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. An estrogen/anti-estrogen-porphyrin conjugate having the structure:

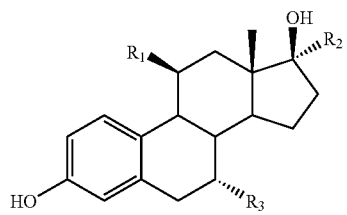

wherein
$R_1$=X—Y—$(CH_2)_n$—X—Y—P, where X=O, NH, S; Y=C(=O), C(=S), n=1–20, $R_2$,$R_3$=H; or
$R_1$=X—Y—$(CH_2)_n$—Y—X—P, where X=O, NH, S; Y=C(=O), C(=S), n=1–20, $R_2$,$R_3$=H; or
$R_1$=Z-$(CH_2)_n$—X—Y—P, where X=O, NH, S; Y=C(=O), C(=S); Z=C≡C, C=CH, $CH_2$—$CH_2$, n=1–20, $R_2$,$R_3$=H; or
$R_2$=X—Y—$(CH_2)_n$—X—Y—P, where X=O, NH, S; Y=C(=O), C(=S), n=1–20, $R_1$,$R_3$=H; or
$R_2$=X—Y—$(CH_2)_n$—Y—X—P, where X=O, NH, S; Y=(=O), C(=S), n=1–20, $R_1$,$R_3$=H; or
$R_2$=Z-$(CH_2)_n$—X—Y—P, where X=O, NH, S; Y=C(=O), C(=S); Z=C≡C, C=CH, $CH_2$—$CH_2$, n=1–20, $R_1$,$R_3$=H; or
$R_3$=X—Y—$(CH_2)_n$—X—Y—P, where X=O, NH, S; Y=C(=O), C(=S), n=1–20, $R_1$,$R_2$=H; or
$R_3$=X—Y—$(CH_2)_n$—Y—X—P, where X=O, NH, S; Y=C(=O), C(=S), n=1–20, $R_1$,$R_2$=H; or
$R_3$=Z—$(CH_2)_n$—X—Y—P, where X=O, NH, S; Y=(=O), C(=S); Z=C≡C, C=CH, $CH_2$—$CH_2$, n=1–20, $R_1$,$R_2$=H;

or the structure:

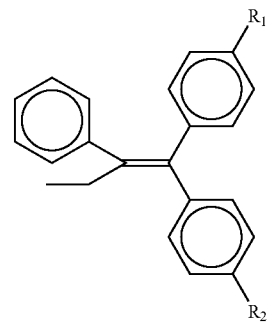

wherein
$R_1$=O—$(CH_2)_2$—$N(CH_3)_2$, $R_2$=X—Y—$(CH_2)_n$—X—Y—P, where X=O, NH, S; Y=$CH_2$, C(=O), C(=S), n=1–20; or
$R_1$=O—$(CH_2)_2$—N$(CH_3)_2$, $R_2$=X—Y—$(CH_2)_n$—Y—X—P, where X=O, NH, S; Y=C(=O), C(=S), n=1–20; or
$R_1$=O—$(CH_2)_2$—N$(CH_3)_2$, $R_2$=Z-$(CH_2)_n$—X—Y—P, where X=O, NH, S; Y=C(=O), C(=S); Z=C≡C, C=CH, $CH_2$—$CH_2$, n=1–20; or
$R_1$=X—Y—$(CH_2)_n$—X—Y—P, where X=O, NH, S; Y=$CH_2$, C(=O), C(=S), n=1–20, $R_2$=H, OH; or
$R_1$=X—Y—$(CH_2)_n$—Y—X—P, where X=O, NH, S; Y=C(=O), C(=S), n=1–20, $R_2$=H, OH; or
$R_1$=Z-$(CH_2)_n$—X—Y—P, where X=O, NH, S; Y=(=O), C(=S); Z=C≡C, C=CH, $CH_2$—$CH_2$, n=1–20, $R_2$=H, OH; or
$R_1$=O—$(CH_2)_2$—N($CH_2$—W)$CH_3$, where W=X—Y—$(CH_2)_n$—X—Y—P, where X=O, NH, S; Y=$CH_2$, C(=O), C(=S), n=1–20, $R_2$=H, OH; or
$R_1$=O—$(CH_2)_2$—N($CH_2$—W)$CH_3$, where W=X—Y—$(CH_2)_n$—X—Y—P, where X=O, NH, S; Y=$CH_2$, C(=O), C(=S), n=1–20, $R_2$=H, OH; or
$R_1$=O—$(CH_2)_2$—N($CH_2$—W)$CH_3$, where W=Z-$(CH_2)_n$—X—Y—P, where X=O, NH, S; Y=C(=O), C(=S); Z=C≡C, C=CH, $CH_2$—$CH_2$, n=1–20, $R_2$=H, OH, and wherein, for either said structure, P=a natural or synthetic porphyrin.

2. The conjugate of claim 1 selected from the group consisting of:

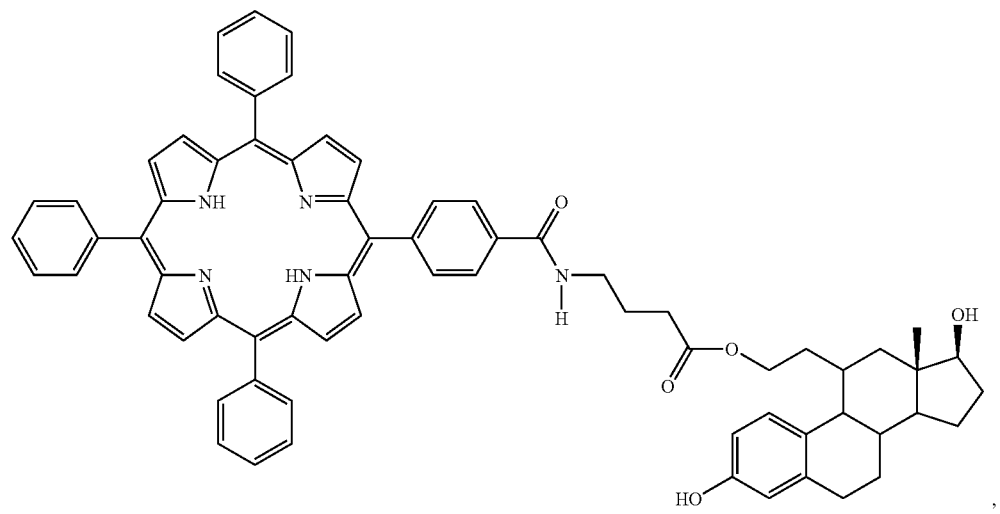
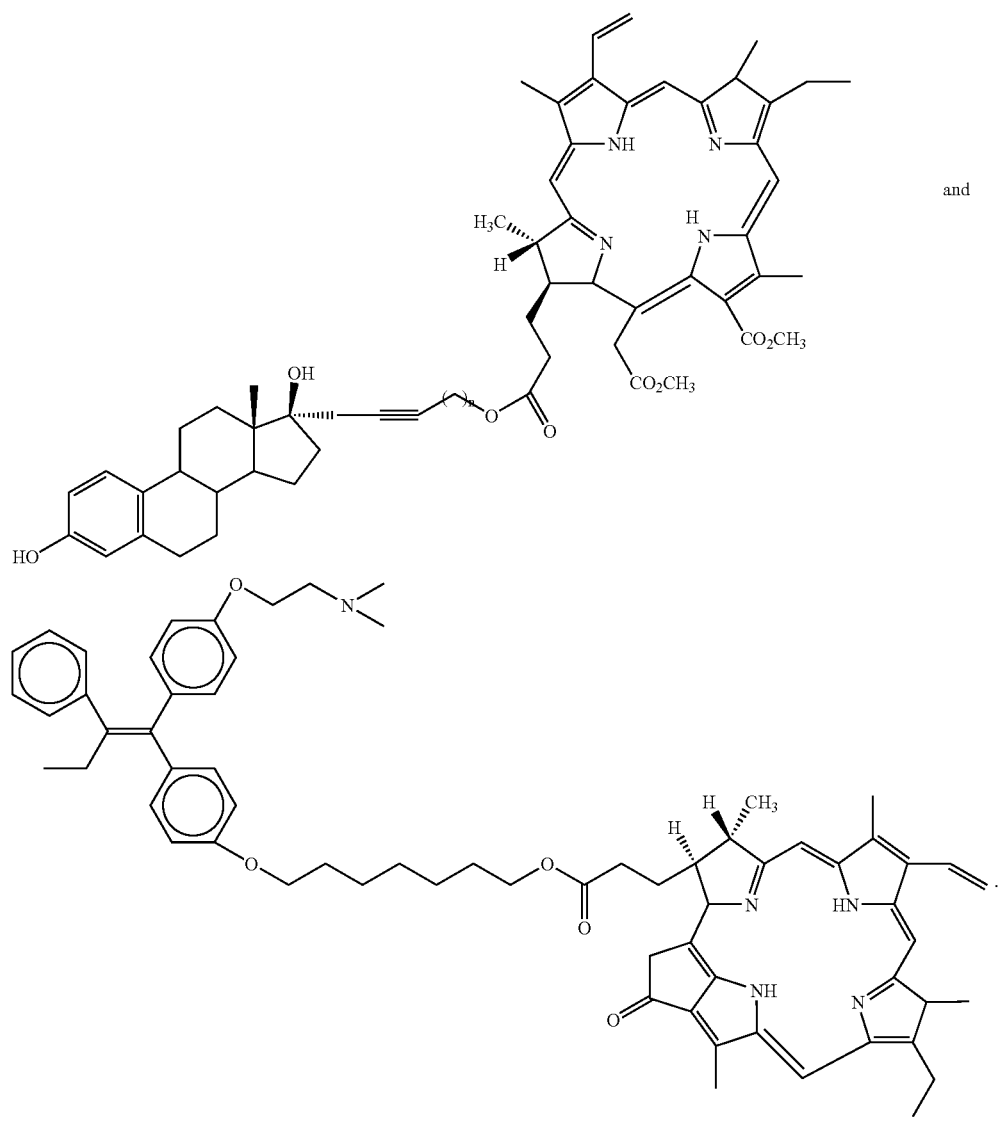

3. A therapeutic composition comprising the estrogen/anti-estrogen-porphyrin conjugate of claim 1 in a pharmaceutically acceptable carrier vehicle.

4. The therapeutic composition of claim 3, wherein said carrier vehicle is physiological saline.

5. The therapeutic composition of claim 3, wherein said carrier vehicle is in the form of liposomes.

6. A method of treating a patient suffering from a cancer of a cell type in which estrogen receptor is expressed, said method comprising the steps of:
 providing the therapeutic composition of claim 3;
 administering to said patient a therapeutically effective dosage of said composition; and
 following said administering step, exposing said patient to a source of light that emits at a wavelength absorbed by the porphyrin portion of said conjugate in said composition.

7. The method of claim 6, wherein said patient is suffering from breast cancer.

8. The method of claim 6, wherein said patient is suffering from ovarian cancer.

9. The method of claim 6, wherein said patient is suffering from endrometrial cancer.

10. The method of claim 6, wherein the conjugate in said therapeutic composition is selected from the conjugates of claim 2.

11. An estrogen/anti-estrogen-porphyrin conjugate having the structure:

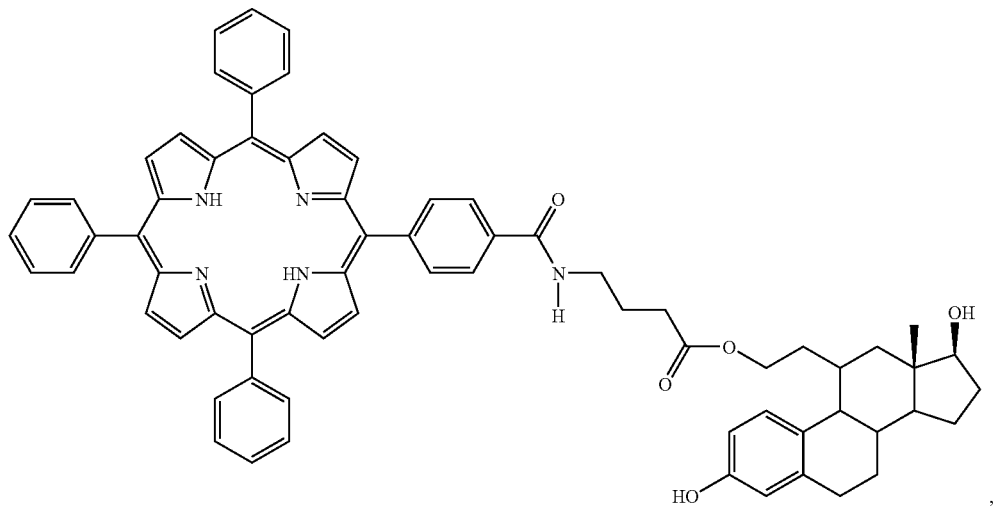

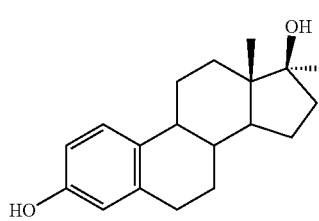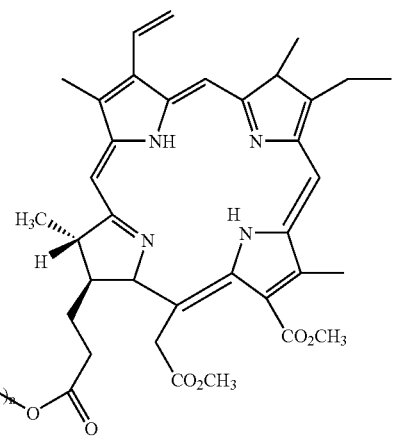

-continued

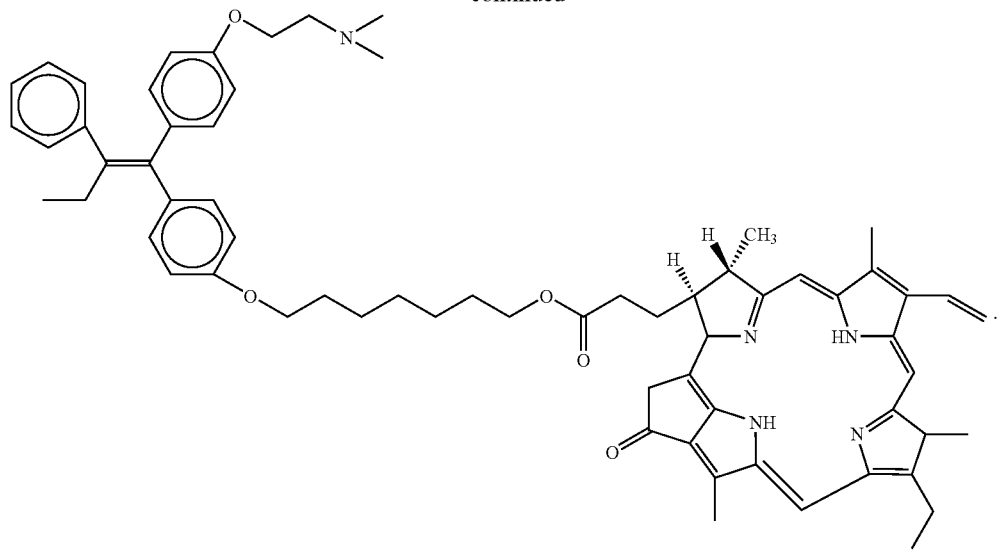

12. A therapeutic composition comprising the estrogen/anti-estrogen-porphyrin conjugate of claim 11 in a pharmaceutically acceptable carrier vehicle.

13. The therapeutic composition of claim 12, wherein said carrier vehicle is physiological saline.

14. The therapeutic composition of claim 12, wherein said carrier vehicle is in the form of liposomes.

15. A method of treating a patient suffering from a cancer of a cell type in which estrogen receptor is expressed, said method comprising the steps of:
   providing the therapeutic composition of claim 12;
   administering to said patient a therapeutically effective dosage of said composition; and
   following said administering step, exposing said patient to a source of light that emits at a wavelength absorbed by the porphyrin portion of said conjugate in said composition.

16. The method of claim 15, wherein said patient is suffering from breast cancer.

17. The method of claim 15, wherein said patient is suffering from ovarian cancer.

18. The method of claim 15, wherein said patient is suffering from endometrial cancer.

* * * * *

UNITED STATES PATENT AND TRADEMARK OFFICE
CERTIFICATE OF CORRECTION

PATENT NO. : 7,038,041 B2 Page 1 of 1
APPLICATION NO. : 10/257081
DATED : May 2, 2006
INVENTOR(S) : Rahul Ray et al.

It is certified that error appears in the above-identified patent and that said Letters Patent is hereby corrected as shown below:

Column 2, line 67, "Y=(=O), C(=S), n=1-20, $R_1,R_3$ = H; or" should read
--Y=C(=O), C(=S), n=1-20, $R_1,R_3$ = H; or--;

Column 3, line 10, "Y=(=O), C(=S); Z=C≡C, C=CH, $CH_2$-$CH_2$," should read
--Y=C(=0), C(=S); Z=C≡C, C=CH, $CH_2$-$CH_2$,--

Column 4, line 17, "Y=(=O), C(=S); Z=C≡C, C=CH, $CH_2$-$CH_2$," should read
--Y=C(=0), C(=S); Z=C≡C, C=CH, $CH_2$-$CH_2$,--

Column 6, line 62, "Compound E" should read --Compound F--;

Column 13, claim 1, line 67, "Y=(=O), C(=S), n=1-20, $R_1,R_3$ = H; or" should read
--Y=C(=O), C(=S), n=1-20, $R_1,R_3$ = H; or--; and Column 14, claim 1, line 11, "Y=(=O), C(=S); Z=C≡C, C=CH, $CH_2$-$CH_2$," should read
--Y=C(=O), C(=S); Z=C≡C, C=CH, $CH_2$-$CH_2$,--.

Signed and Sealed this

Fourth Day of December, 2007

JON W. DUDAS
*Director of the United States Patent and Trademark Office*